United States Patent [19]
Souda et al.

[11] Patent Number: 5,162,317
[45] Date of Patent: Nov. 10, 1992

[54] PYRIDINIUM SALT AND PHARMACOLOGICAL COMPOSITION CONTAINING THE SAME

[75] Inventors: Shigeru Souda; Shuhei Miyazawa; Norihiro Ueda; Katsuya Tagami; Seiichiro Nomoto; Makoto Okita; Naoyuki Shimomura; Toshihiko Kaneko; Masatoshi Fujimoto; Manabu Murakami; Kiyoshi Oketani; Hideaki Fujisaki; Hisashi Shibata; Tsuneo Wakabayashi, all of Ibaraki, Japan

[73] Assignee: Esai Co., Ltd., Tokyo, Japan

[21] Appl. No.: 445,664

[22] PCT Filed: May 11, 1989

[86] PCT No.: PCT/JP89/00482

§ 371 Date: Dec. 5, 1989

§ 102(e) Date: Dec. 5, 1989

[87] PCT Pub. No.: WO89/10927

PCT Pub. Date: Nov. 16, 1989

[30] Foreign Application Priority Data

May 12, 1988 [JP] Japan ................. 63-115494
May 12, 1988 [JP] Japan ................. 63-115495

[51] Int. Cl.$^5$ ............. A61K 31/54; C07D 285/20
[52] U.S. Cl. ..................... 514/222.8; 544/9
[58] Field of Search .................. 544/9; 514/222.8

[56] References Cited

U.S. PATENT DOCUMENTS 4,636,499 1/1987 Brändström et al. ............ 514/222
4,769,456 9/1988 Nohara et al. ..................... 544/9

Primary Examiner—Mukund J. Shah
Assistant Examiner—Matthew V. Grumbling
Attorney, Agent, or Firm—Nixon & Vanderhye

[57] ABSTRACT

A pyridinium salt useful as an antiulcer agent, defined by formula (I) is disclosed. It includes a sulphenamide compound and a pyridinium compound. J is benzimidazole, K is —S— or —SSR— and Z is hydroxy or alkoxy.

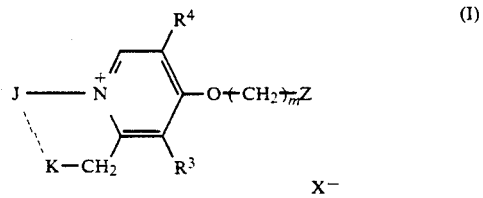

6 Claims, No Drawings

PYRIDINIUM SALT AND PHARMACOLOGICAL COMPOSITION CONTAINING THE SAME

FIELD OF THE INDUSTRIAL APPLICATION

This invention relates to a pyridinium salt having an antiulcer effect.

BACKGROUND OF THE INVENTION

It is believed that peptic ulcers such as gastric and duodenal ulcers are formed when aggressive factors such as acid and pepsin and protective factors such as mucosa-resistance, mucus, blood and duodenal control are out of balance and thus autolysis is induced.

Peptic ulcers are to be medically treated as a rule. Therefore medicinal treatments therefor have been attempted so far. Examples of the antiulcer drugs which are commonly used today include cimetidine and ranitidine, each based on the histamine $H_2$ receptor antagonism. However it has been reported that these drugs are accompanied by some side effects, for example, an antiandrogenic effect or an inhibitive effect on hepatic metabolic enzyme activity.

Under these circumstances, it is recently suggested that an inhibitor for $H^+-K^+ATPase$, which specifically occurs in gastric wall cells, would serve as an excellent inhibitor for acid secretion.

SUMMARY OF THE INVENTION

The invention provides a new pyridinium salt having the formula (I):

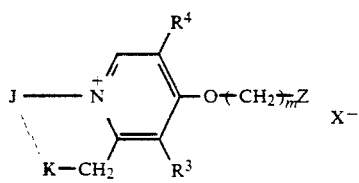

(I)

in which R3 and R4 each are hydrogen or a lower alkyl, m is an integer of 2 to 10, Z is —OR5 or —O—(CH2)n—OR6, R5 is hydrogen, a lower alkyl, an aryl or an aryl alkyl, R6 is hydrogen, a lower alkyl, an aryl or an arylalkyl, n is an integer of 1 to 3, X is a pharmacologically acceptable anion, K is (1) —S— or (2) —S—S—R, R is an organic group which may have a substituent, J is a benzoimidazole ring which may have a substituent(s), — shows a bond thereby to connect with the nitrogen of the benzimidazole or no bond, provided that (1) when K is —S—, J is a group having the formula:

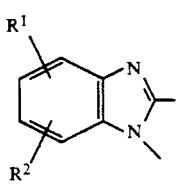

in which R1 and R2 each are hydrogen, a lower alkyl, a lower alkoxy, a halogenated lower alkyl, a lower alkoxycarbonyl, carboxyl or a halogen, (2) when K is —S—S—R, J is a group having the formula:

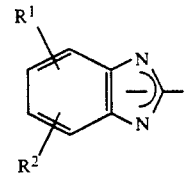

and X does not exist.

The pyridinium salt as defined above includes two embodiments. One is a sulphenamide derivative having the formula (I a) and the other is a pyridinium salt having the formula (I-b):

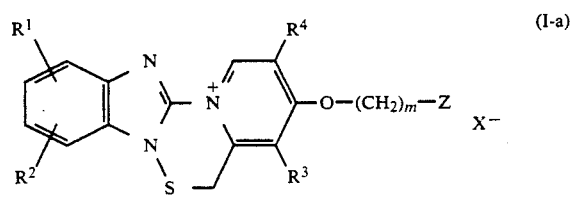

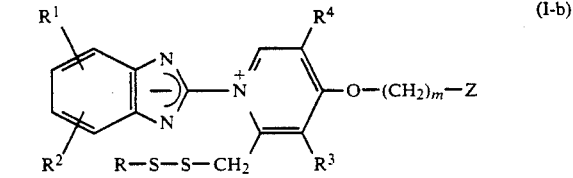

It is preferred that in the formula (I), (I-a) and (I-b), R3 is methyl and R4 is hydrogen. Moreover Z is preferably —OR5. m is preferably 3. R5 is preferably methyl.

The invention provides a pharmacological composition which comprises a pharmacologically effective amount of the pyridinium salt having the formula (I) and a pharmacologically acceptable carrier.

The invention will be explained in view of the embodiments (I-a) and (I-b).

Compound (I-a)

The target compound of the present invention is a sulphenamide derivative represented by the following general formula (I):

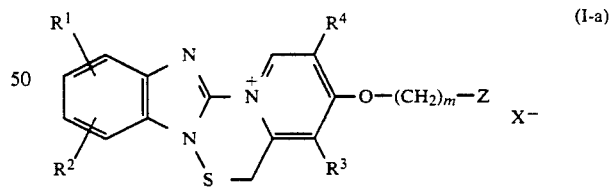

wherein
R¹ and R² may be the same or different from each other and each represents a hydrogen atom, a lower alkyl, a lower alkoxy, a halogenated lower alkyl, a lower alkoxycarbonyl or a carboxyl group or a halogen atom;

R³ and R⁴ represent each a hydrogen atom or a lower alkyl group;

m is an integer of 2 to 10;

Z is a group represented by the formula —OR⁵, wherein R⁵ represents a hydrogen atom or a lower alkyl, an aryl or an arylalkyl group, or a group represented by the formula —O—(CH₂)ₙ—O—R⁶, wherein n is an integer of 1 to 3 and $R^6$ represents a hydrogen atom or a lower alkyl, an aryl or an arylalkyl group; and $X^-$ is a pharmacologically acceptable anion.

Accordingly, it is an object of the present invention to provide a novel sulphenamide derivative which is effective as an antiulcer drug, a process for the preparation of the same and a novel antiulcer drug containing the same.

Examples of the lower alkyl groups $R^1$, $R^2$, $R^3$, $R^4$, $R^5$ and $R^6$ of the compound (I) of the present invention which is defined above include straight-chain and branched alkyl groups carrying one to six carbon atoms, such as methyl, ethyl, n-propyl, n-butyl, isopropyl, isobutyl, 1-methylpropyl, ter-butyl, n-pentyl, 1-ethylpropyl, isoamyl and n-hexyl groups. Among these groups, methyl and ethyl groups are the most preferable.

The terms "lower alkoxy group", "halogenated lower alkyl group" and "lower alkoxycarbonyl group" used in the definition of the $R^1$ and $R^2$ groups in the general formula (I) refer to those derived from the abovementioned lower alkyl groups. Among these groups, those derived from methyl, ethyl and propyl groups are the most preferable. Particular examples of the lower alkoxy group include methoxy, ethoxy and propoxy groups. Particular examples of the lower alkoxycarbonyl group include methoxycarbonyl and ethoxycarbonyl groups. A preferable example of the halogenated lower alkyl group is a trifluoromethyl group.

The term "halogen atom" used in the definition of the $R^1$ and $R^2$ groups refers to a chlorine, bromine, iodine or fluorine atom.

Preferable examples of the $R^1$ and $R^2$ groups include a hydrogen atom, a lower alkyl group such as a methyl group, a lower alkoxy group such as a methoxy group and a trifluoromethyl group. It is further preferable that either one of them is a lower alkyl or a lower alkoxy group and the other is a hydrogen atom; or that both of the $R^1$ and $R^2$ groups are hydrogen atoms.

The term "aryl group" used in the definition of the $R^5$ and $R^6$ groups refers to, for example, a phenyl, tolyl, xylyl or naphthyl group which is optionally substituted with, for example, a lower alkoxy group such as a methoxy or an ethoxy group, a hydroxyl group or a halogen atom.

The term "arylalkyl group" used in the definition of the $R^5$ and $R^6$ group refers to, for example, a benzyl or phenetyl group.

m is an integer of 2 to 10. It is the most preferable that m is 3.

$X^-$ represents a pharmacologically acceptable anion without limitation. Examples thereof include $Cl^-$, $Br^-$, $I^-$, $BF_4^-$, $PF_6^-$, $HSO_4^-$, $SO_4^{2-}$, $CH_3SO_3^-$,

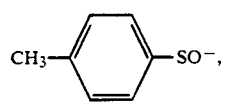

$PO_4^-$, $ClO_4^-$ and $AuCl_4^-$.

Now a typical process for the preparation of the compound of the present invention will be described.

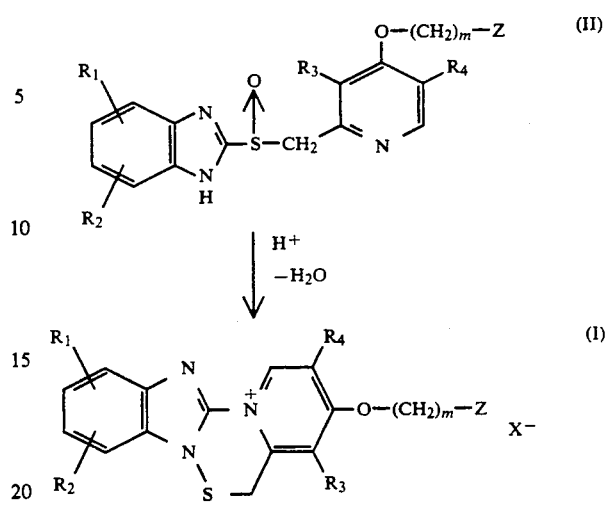

Namely, a pyridine derivative of the general formula (II) is reacted under heating in the presence of an acid in a conventional manner to thereby give the aimed compound (I). Examples of the acid include tetrafluoroboric acid, hexafluorophosphoric acid, sulfuric acid, hydrochloric acid, oxalic acid, iodic acid, perchloric acid, methanesulfonic acid and toluenesulfonic acid. In order to achieve a desirable result, the acid is to be used in an amount of one to three equivalents.

Examples of the solvent commonly used in the above reaction include ethers such as ether and tetrahydrofuran, alcohols such as methyl alcohol and ethyl alcohol, water, chloroform, dichloromethane, acetone, acetonitrile, dimethylformamide, dimethyl sulfoxide and mixtures thereof. The reaction may be carried out at $-40°$ to approximately $100°$ C., preferably approximately $30°$ to $50°$ C. The reaction period ranges from several minutes to several hours.

The pyridine derivative to be used as the starting material in the above reaction may be prepared according to a method described in, for example, Japanese Patent Application No. 286668/1987.

More specifically, it may be prepared by the following process A or B.

Process A:

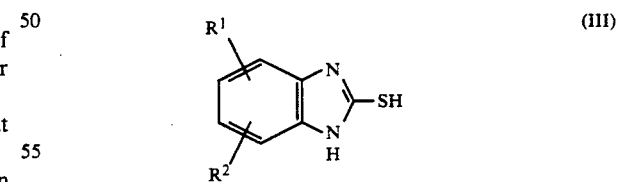

wherein $R^1$ and $R^2$ are as defined above;

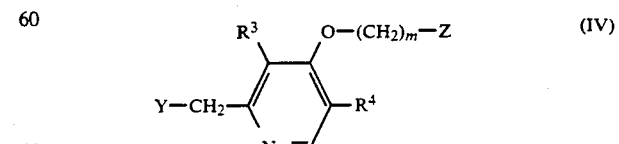

wherein $R^3$, $R^4$, m and Z are as defined above; and Y represents a halogen atom or a sulfonyloxy group;

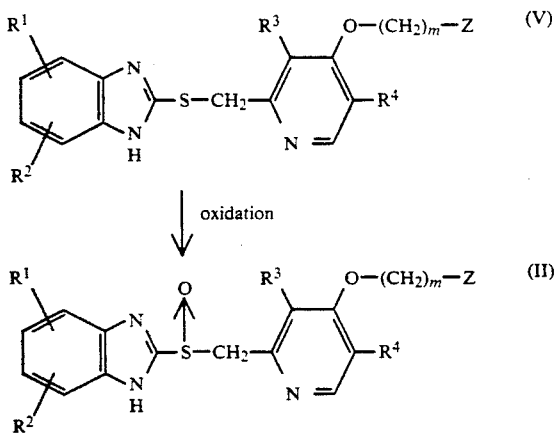

Namely, the compound of the general formula (III) is reacted with a halide or a sulfonate of the general formula (IV) to thereby give the compound (V).

The term "halogen atom" used in the definition of the Y group refers to, for example, a chlorine, bromine or iodine atom, while the term "sulfonyl group" to, for example, an alkylsulfonyloxy group such as a methylsulfonyloxy or ethylsulfonyloxy group and an aromatic sulfonyloxy group such as a benzenesulfonyloxy or tosyloxy group.

In order to achieve a perferable result, the reaction is to be carried out in the presence of an acid binder. Examples of the acid binder include alkali metal carbonates and hydrogencarbonates such as potassium carbonate, sodium carbonate and sodium hydrogencarbonate; alkali hydroxides such as sodium hydroxide and potassium hydroxide; and organic amines such as pyridine and triethylamine. Examples of the solvent to be used in the reaction include alcohols such as methyl alcohol and ethyl alcohol, tetrahydrofuran, dioxane, dimethylformamide, dimethyl sulfoxide and mixtures thereof with water.

The reaction may be carried out at a temperature ranging from $-40°$ C. to the boiling point of the solvent. It may be preferably carried out at approximately $0°$ to $60°$ C.

The compound (V) thus obtained is then oxidized. Thus the pyridine derivative (II), which is the starting compound in the present invention, may be readily obtained.

The oxidation may be conducted in a conventional manner by using an oxidizing agent such as hydrogen peroxide, peracetic acid, m-chloroperbenzoic acid, sodium hypochlorite or sodium bromite. The solvent to be used in this reaction may be selected from among, for example, dichloromethane, chloroform, benzene, toluene, methanol and ethanol.

The reaction temperature may range from $-70°$ C. to the boiling point of the solvent. It is preferable to conduct the reaction at $-60$ to $25°$ C.

Process B:

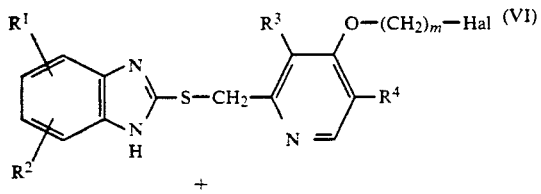

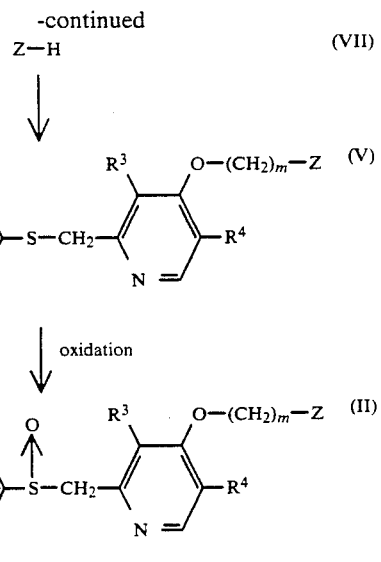

wherein $R^1$, $R^2$, $R^3$, $R^4$, m and Z are as defined above; and Hal represents a halogen atom.

Namely, the halide of the general formula (VI) is reacted with the compound of the general formula (VII), which may be an alcohol, a thiol or an amine, to thereby give the compound of the general formula (V). Then the compound (V) is oxidized in the same manner as the one described above to thereby give the compound of the general formula (II). Similar to the process A, this reaction is preferably carried out in the presence of an acid binder. Examples of the acid binder include alkali metal carbonates such as potassium carbonate and sodium carbonate and hydrogen-carbonates; alkali hydroxides such as sodium hydroxide and potassium hydroxide; and triethylamine. The solvent to be used in the reaction may be selected from among, for example, ethers such as tetrahydrofuran and dioxane; ketones such as acetone and methyl ethyl ketone; benzene derivatives such as benzene, toluene and xylene; acetonitrile, dimethylformamide, dimethyl sulfoxide and hexamethylphosphoric triamide. The reaction may be carried out within a temperature range from ice-cooling to the boiling point of the solvent.

To further illustrate the effects of the present invention, the following pharmacological test example on a typical compound of the present invention will be given.

PHARMACOLOGICAL TEST EXAMPLE

Inhibition effect on $H^+-K^+$ATPase activity (1) Preparation of $H^+-K^+$ATPase The enzyme $H^+-K^+$ATPase was prepared from the fundus ventriculi gland of fresh swine gastric mucosa by a modified method of Saccomani et al. (Biochem. and Biophys. Acta., 464, 313 (1977)).

(2) Determination of $H^+-K^+$ATPase activity

Various concentrations of the compounds of the present invention were incubated together with 10 μg protein/ml of the $H^+-K^+$ATPase in a 40 mM Tris HCl buffer (pH 7.40) at 37° C. for 30 minutes. Then 15 mM KCl was added thereto. Ten minutes thereafter, an ATPase reaction between 3 mM of $MgCl_2$ and ATP was started. Ten minutes thereafter, the liberated inorganic phosphoric acid was determined according to Yoda and Hokin's method (cf. Biochem. Biophys. Res., Com., 40, 880 (1970)).

The test compound was 3-(3-methoxy)propoxy-4-methyl-5H-pyrido[1',2':4.5][1.2.4.]thiazino[2.3-a]-benzimidazol-13-ium tetrafluoroborate (the compound of Example 1). This compound was dissolved in methanol prior to the test.

The inhibition effect (%) was calculated by dividing the difference between the data of the test group and that of the control group, to which solvent was added exclusively, by the data of the control group.

The $IC_{50}(M)$ of the above test compound was $4.4 \times 10^{-7}$, while that of a control compound (Omeprazole) was $1.1 \times 10^{-5}$.

The above pharmacological test obviously indicates that the compound of the present invention has an intense inhibition effect on $H^+-K^+ATPase$.

Accordingly, the compound of the present invention, which has an excellent effect of inhibiting acid secretion based on the intense $H^+-K^+ATPase$ inhibition effect, is useful in the treatment and prevention of human and animal peptic ulcers.

Compound (I-b)

The target compound of the present invention is a pyridinium derivative represented by the following general formula (I) and a pharmacologically acceptable salt thereof:

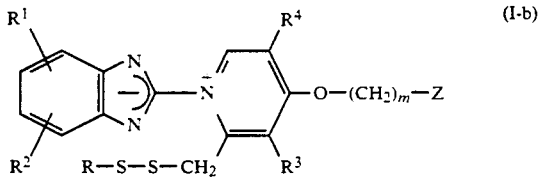

wherein
$R^1$ and $R^2$ may be the same or different from each other and each represents a hydrogen atom, a lower alkyl, a lower alkoxy, a halogenated lower alkyl, a lower alkoxycarbonyl or a carboxyl group or a halogen atom;
$R^3$ and $R^4$ represent each a hydrogen atom or a lower alkyl group;
m is an integer of 2 to 10;
Z is a group represented by the formula $-OR^5$, wherein $R^5$ represents a hydrogen atom or a lower alkyl, an aryl or an arylalkyl group, or a group represented by the formula $-O-(CH_2)_n-O-R^6$, wherein n is an integer of 1 to 3 and $R^6$ represents a hydrogen atom or a lower alkyl, an aryl or an arylalkyl group; and
R represents an optionally substituted organic group.

Accordingly, it is an object of the present invention to provide a novel pyridinium derivative which is effective as an antiulcer drug, a process for the preparation of the same and a novel antiulcer drug containing the same.

The term "lower alkyl group" used in the definition of the R', $R^2$, $R^3$, $R^4$, $R^5$ and $R^6$ in the compound (I) of the present invention refers to a straight-chain or branched alkyl group carrying one to six carbon atoms. Examples thereof include methyl, ethyl, n-propyl, n-butyl, isopropyl, isobutyl, 1-methylpropyl, ter-butyl, n-pentyl, 1-ethylpropyl, isoamyl and n-hexyl groups. Among these groups, methyl and ethyl groups are particularly preferable.

The terms "lower alkoxy group", "halogenated lower alkyl group" and "lower alkoxycarbonyl group" used in the definition of the $R^1$ and $R^2$ groups in the general formula (I) refer to those derived from the abovementioned lower alkyl groups. Among these groups, those derived from methyl, ethyl and propyl groups are the most preferable. Particular examples of the lower alkoxy group include methoxy, ethoxy and propoxy groups. Particular examples of the lower alkoxycarbonyl group include methoxycarbonyl and ethoxycarbonyl groups. A preferable example of the halogenated lower alkyl group is a trifluoromethyl group.

The term "halogen atom" used in the definition of the $R^1$ and $R^2$ groups refers to a chlorine, bromine, iodine or fluorine atom.

Preferable examples of the $R^1$ and $R^2$ groups include a hydrogen atom, a lower alkyl group such as a methyl group, a lower alkoxy group such as a methoxy group and a trifluoromethyl group. It is further preferable that either one is a lower alkyl or a lower alkoxy group and the other is a hydrogen atom; or that both of the $R^1$ and $R^2$ groups are hydrogen atoms.

The term "aryl group" used in the definition of the $R^5$ and $R^6$ groups refers to, for example, a phenyl, tolyl, xylyl or naphthyl group which is optionally substituted by, for example, a lower alkoxy group such as a methoxy or an ethoxy group, a hydroxyl group or a halogen atom.

The term "arylalkyl group" used in the definition of the $R^5$ and $R^6$ group refers to, for example, a benzyl or phenetyl group.

m is an integer of 2 to 10. It is the most preferable that m is 3.

R is an optionally substituted organic group. Particular examples thereof include optionally substituted lower alkyl, cycloalkyl, aryl, arylalkyl, alkenyl, heteroaryl and heteroarylalkyl groups.

The term "lower alkyl group" has the same meaning as the one described in the above definition of $R^1$, $R^2$, $R^3$, $R^4$, $R^5$ and $R^6$. Thus, examples thereof include straight-chain and branched alkyl groups carrying one to six carbon atoms, such as methyl, ethyl, n-propyl, n-butyl, isopropyl, isobutyl, 1-methylpropyl, ter-butyl, n-pentyl, 1-ethylpropyl, isoamyl and n-hexyl groups. Among these groups, methyl, ethyl, n-propyl and isopropyl groups are the most preferable.

Examples of the aryl group include phenyl, naphthyl and tolyl groups. Examples of the arylalkyl group include phenethyl and benzyl groups. As the alkenyl group, those carrying three to six carbon atoms are preferable.

Examples of the heteroaryl group, include five-and six-membered rings containing one to four sulfur, nitrogen and/or oxygen atom(s) which are either the same or different from each other. These rings may be condensed with each other to thereby form a condensed heterocycle. Alternately, they may be condensed with a benzene ring. Preferable examples thereof include pyridyl, pyrimidyl, pyrazyl, piperidyl, pyrazolyl, thiazolyl, oxazolyl, imidazolidinyl and benzothiazolyl groups.

These organic groups may be optionally substituted with, for example, lower alkyl group(s), halogen atom(s), trifluoromethyl group(s) or lower alkoxy group(s).

Now a typical process for the presentation of the compound of the present invention will be described.

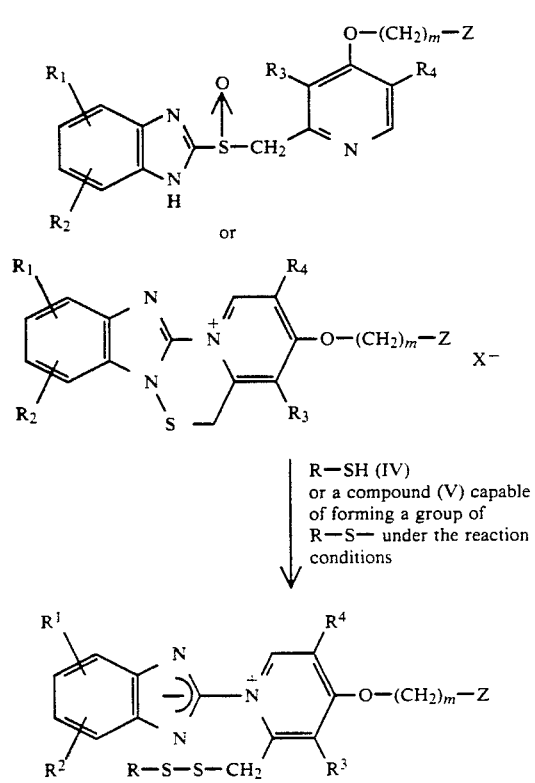

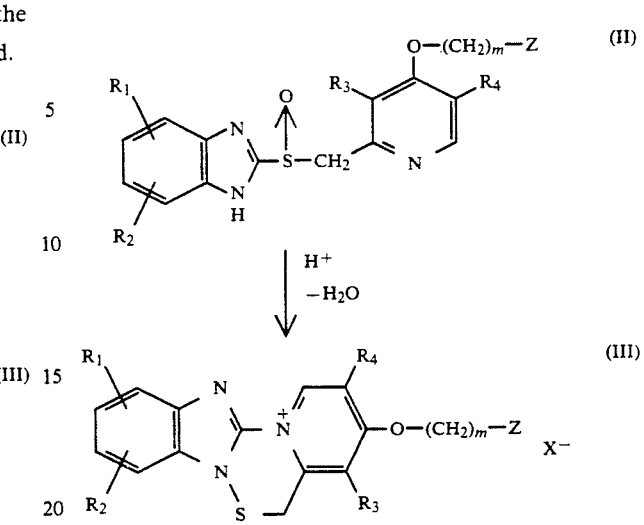

wherein $R^1$, $R^2$, $R^3$, $R^4$, m, R and Z are as defined above.

Namely, the compound of the general formula (II) or (III) is reacted with the compound of the general formula R—SH (IV) or the compound (V), which is capable of forming an R—S— group under the reaction conditions, preferably in the presence of an acid. Thus the aimed compound (I) can be obtained.

This reaction is carried out at $-40°$ to $100°$ C., preferably at room temperature, for several minutes to several hours.

Examples of the acid to be used include tetrafluoroboric acid, hexafluorophosphoric acid, hydrochloric acid, perchloric acid and methanesulfonic acid. These acids are usually employed in an amount of one to three equivalents. Examples of the solvent to be used in the above reaction include ether, tetrahydrofuran, methyl alcohol, ethyl alcohol, water, chloroform, dichloromethane, acetone, acetonitrile, dimethylformamide, dimethyl sulfoxide and mixtures thereof.

The compound (III) which is the starting material may be prepared by, for example, the following method.

Namely, the pyridine derivative of the general formula (II) is reacted under heating in the presence of an acid in a conventional manner to thereby give the compound (III). Examples of the acid include tetrafluoroboric acid, hexafluorophosphoric acid, sulfuric acid, hydrochloric acid, oxalic acid, iodic acid, perchloric acid, methanesulfonic acid and toluenesulfonic acid. In order to achieve a preferable result, these acids are to be used in an amount of one to three equivalents.

Examples of the solvent commonly used in the above reaction include ethers such as ether and tetrahydrofuran, alcohols such as methyl alcohol and ethyl alcohol, water, chloroform, dichloromethane, acetone, acetonitrile, dimethylformamide, dimethyl sulfoxide and mixtures thereof. The reaction temperature ranges from $-40°$ to approximately $100°$ C., preferably approximately $30°$ to $50°$ C. The reaction period ranges from several minutes to several hours.

The pyridine derivative (II) to be used as the starting material in the above reaction may be obtained by, for example, a method described in Japanese Patent Application No. 286668/1987.

Namely, it may be obtained by the following process A or B.

Process A:

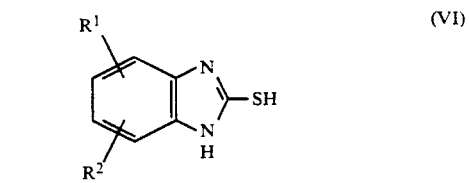

wherein $R^1$ and $R^2$ are as defined above;

+

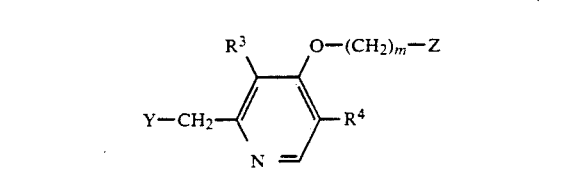

wherein $R^3$, $R^4$, m and Z are as defined above; and Y represents a halogen atom or a sulfonyloxy group;

-continued

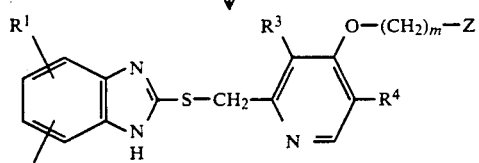
(VIII)

↓ oxidation

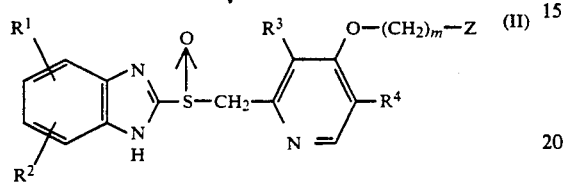
(II)

Namely, the compound of the general formula (VI) is reacted with a halide or sulfonate of the general formula (VII) to thereby give the compound (VIII).

The term "halogen atom" used in the definition of the Y group refers to, for example, a chlorine, bromine or iodine atom, while the term "sulfonyl group" to, for example, an alkylsulfonyloxy group such as a methylsulfonyloxy or ethylsulfonyloxy group and an aromatic sulfonyloxy group such as a benzenesulfonyloxy or tosyloxy group.

In order to achieve a perferable result, the reaction is to be carried out in the presence of an acid binder. Examples of the acid binder include alkali metal carbonates and hydrogencarbonates such as potassium carbonate, sodium carbonate and sodium hydrogencarbonate; alkali hydroxides such as sodium hydroxide and potassium hydroxide; and organic amines such as pyridine and triethylamine. Examples of the solvent to be used in the reaction include alcohols such as methyl alcohol and ethyl alcohol, tetrahydrofuran, dioxane, dimethylformamide, dimethyl sulfoxide and mixtures thereof with water.

The reaction may be carried out at a temperature ranging from −40° C. to the boiling point of the solvent. It may be preferably carried out at approximately 0° to 60° C.

The compound (VIII) thus obtained is then oxidized. Thus the pyridine derivative (II), which is the starting compound in the present invention, may be readily obtained.

The oxidation may be conducted in a conventional manner by using an oxidizing agent such as hydrogen peroxide, peracetic acid, m-chloroperbenzoic acid, sodium hypochlorite or sodium bromite. The solvent to be used in this reaction may be selected from among, for example, dichloromethane, chloroform, benzene, toluene, methanol and ethanol.

The reaction temperature may range from −70° C. to the boiling point of the solvent. It is preferable to conduct the reaction at −60° to 25° C.

Process B:

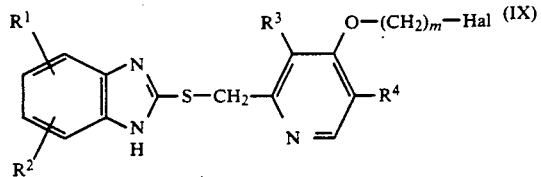
(IX)

+

Z—H (X)

↓

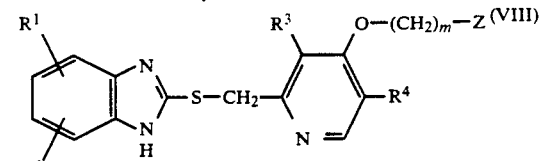
(VIII)

↓ oxidation

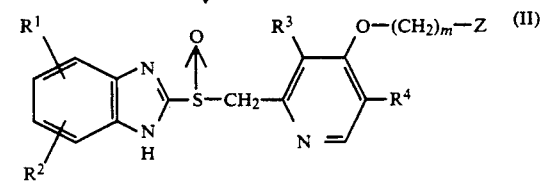
(II)

wherein $R^1$, $R^2$, $R^3$, $R^4$, m and Z are as defined above; and Hal represents a halogen atom.

Namely, the halide of the general formula (IX) is reacted with the compound of the general formula Z—H (X), which may be an alcohol, a thiol or an amine, to thereby give the compound of the general formula (VIII). Then the compound (VIII) is oxidized in the same manner as the one described above to thereby give the compound of the general formula (II). Similar to the process A, this reaction is preferably carried out in the presence of an acid binder. Examples of the acid binder include alkali metal carbonates such as potassium carbonate and sodium carbonate and hydrogencarbonates; alkali hydroxides such as sodium hydroxide and potassium hydroxide; and triethylamine. The solvent to be used in the reaction may be selected from among, for example, ethers such as tetrahydrofuran and dioxane; ketones such as acetone and methyl ethyl ketone; benzene derivatives such as benzene, toluene and xylene; acetonitrile, dimethylformamide, dimethyl sulfoxide and hexamethylphosphoric triamide. The reaction may be carried out within a temperature range from icecooling to the boiling point of the solvent.

To further illustrate the effects of the present invention, the following pharmacological test example on a typical compound of the present invention will be given.

PHARMACOLOGICAL TEST EXAMPLE

Inhibition effect on $H^+$—$K^+$ATPase activity (1) Preparation of $H^+$—$K^+$ATPase The enzyme $H^+$—$K^+$ATPase was prepared from the fundus ventriculi gland of fresh swine gastric mucosa by a modified method of Saccomani et al. (Biochem. and Biophys. Acta., 464, 313 (1977)).

(2) Determination of $H^+$—$K^+$ATPase activity

Various concentrations of the compounds of the present invention were incubated together with 10 μg protein/ml of the $H^+—K^+$ATPase in a 40 mM Tris HCl buffer (pH 7.40) at 37° C. for 30 minutes. Then 15 mM KCl was added thereto. Ten minutes thereafter, an ATPase reaction between 3 mM of MgCl and ATP was started. Ten minutes thereafter, the liberated inorganic phosphoric acid was determined according to Yoda and Hokin's method (cf. Biochem. Biophys. Res., Com., 40, 880 (1970)).

The test compound was 2-[2-(ethyldithiomethyl)4-(3-methoxy)propoxy-3-methyl-1-pyridinio)benzimidazolide (the compound of Example 1). This compound was dissolved in methanol prior to the test.

The inhibition effect (%) was calculated by dividing the difference between the data of the test group and that of the control group, to which solvent was added exclusively, by the data of the control group.

The $IC_{50}(M)$ of the above test compound was higher than $1\times 10^{-5}$.

The above pharmacological test obviously indicates that the compound of the present invention has an intense inhibition effect on $H^+—^K+$ATPase.

Accordingly, the compound of the present invention, which has an excellent effect of inhibiting acid secretion based on the intense $H^+—K^+$ATPase inhibition effect, is useful in the treatment and prevention of human and animal peptic ulcers.

Application of the compound (I) of the invention

When the compound of the present invention is to be administered as a therapeutic or preventive agent for peptic ulcer, it may be orally administered in the form of, for example, powders, granules, capsules or syrups. Alternately, it may be parenterally administered in the form of, for example, suppositories, injections, external preparations or intravenous drips. The dose may vary depending on the condition, age and ulcer type of the patient. Generally speaking, it may be administered in a dose of approximately 0.01 to 200 mg/kg/day, preferably 0.05 to 50 mg/kg/day and still preferably 0.1 to 10 mg/kg/day in one to several portions.

It may be formulated in a conventional manner by using conventional pharmacological carriers.

When a solid preparation for oral administration is to be produced, for example, the active component is mixed with a filler as well as a binder, a disintegrating agent, a lubricant, a colorant and/or a corrigent, if required. The obtained mixture is then formulated into tablets, coated tablets, granules, powders or capsules in a conventional manner.

Examples of the filler include lactose, corn starch, white sugar, glucose, sorbitol, crystalline cellulose and silicon dioxide. Examples of the binder include polyvinyl alcohol, polyvinyl ether, estylcellulose, methylcellulose, gum arabic, tragacanth, gelatin, shellac, hydroxypropyl-cellulose, hydroxypropylstarch and polyvinylpyrrolidone. Examples of the disintegrating agent include starch, agar, gelatin powder, crystalline cellulose, calcium carbonate, sodium hydrogencarbonate, calcium citrate, dextrin and pectin. Examples of the lubricant include magnesium stearate, talc, polyethylene glycol, silica and hardened vegetable oils. As the colorant, pharmacologically acceptable ones may be employed. Examples of the corrigent include cocoa powder, mentha herb, aromatic powder, mentha oil, borneol and cinnamon powder. Needless to say, these tablets or granules may be coated with, for example, sugar or gelatin.

When an injection is to be produced, the active component is mixed with various additives such as a pH modifier, a buffer, a stabilizer or a solubilizing agent, if required. Thus a subcutaneous, intramuscular or intravenous injection is obtained.

EXAMPLES OF THE COMPOUND I-a

To further illustrate the present invention, and not by way of limitation, the following Examples will be given.

EXAMPLE 1

3-(3-Methoxy)propoxy-4-methyl-5H-pyrido[1',2':4.5][1.2.4]thiaziano[2.3-a]benzimidazol-13-ium tetrafluoroborate

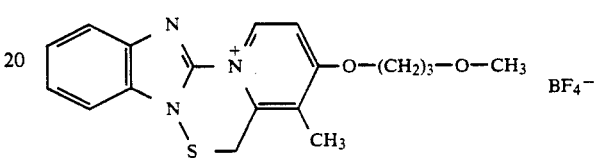

Process a:

0.36 g of 2-[4-(3-methoxy)-propoxy-3-methylpyridin-2-yl]methylsulfinyl-1H-benzimidazole, 5 ml of methanol and 0.19 g of 85% tetrafluoroboric acid ether complex were mixed together. The resulting mixture was stirred at 40° C. for ten minutes and then further stirred under ice-cooling for 30 minutes. The crystals thus precipitated were collected by filtration. Thus 0.32 g of the aimed compound was obtained in the form of yellow crystals.

Process b:

0.38 g of 2-[4-(3-methoxy)-propoxy-3-methylpyridin-2-yl]methylsulfinyl-1H-benzimidazole sodium salt, 5 ml of methanol and 0.38 g of 85% tetrafluoroboric acid/ether complex were mixed together. The resulting mixture was stirred at 40° C. for ten minutes and then further stirred under ice-cooling for 30 minutes. The crystals thus precipitated were collected by filtration. Thus 0.32 g of the aimed compound was obtained in the form of yellow crystals.

m.p.: 141–143° C. (decomp.)

$^1$H-NMR (90MHz, $CDCL_3$-$CD_3OD$) δ; 2.22(2H, m), 2.51(3H, s), 3.36(3H, s), 3.59(2H, t, J=6.3Hz), 4.58(2H, t, J=6.3 Hz), 4.85(2H, s), 7.23~7.77(4H, m), 7.64(1H, d, J=7.2Hz), 9.37(1H, d, J=7.2 Hz).

EXAMPLE 2

3-(3-Methoxy)propoxy-4-methyl-5H-pyrido[1'.2':4.5.][1.2.4]-thiaziazino[2.3-a]benzimidazol-13-ium hexafluorophosphate

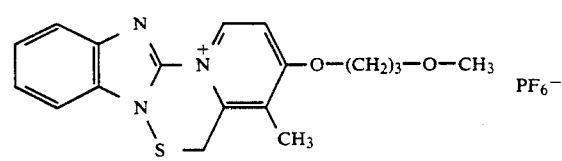

0.38 g of 2-[4-(3-methoxy)propoxy-3-methylpyridin-2-yl]-methylsulfinyl-1H-benzimidazole sodium salt, 5 ml of methanol and 0.48 g of 60% hexafluorophosphoric acid were mixed together. The resulting mixture was stirred at 40° C. for ten minutes and then further stirred under ice-cooling for 30 minutes. The crystals thus precipitated were collected by filtration. Thus 0.30 g of the aimed compound was obtained in the form of yellow crystals.

m.p.: 143–145° C. (decomp.)

$^1$H-NMR(90MHz, CDCL$_3$-DMSO d$_6$) δ; 2.25(2H, m), 2.53(3H, s) 3.38(3H, s), 3.62(2H, t, J=6.3Hz), 4.65(2H, t, J=6.3Hz), 4.99(2H, s), 7.37~7.93(4H, m), 7.81(1H, d, J=7.2Hz), 9.57(1H, d, J=7.2Hz).

EXAMPLE 3A+3B

9-Methoxy-3-(3-methoxy)propoxy-4-methyl-5H-pyrido[1′.2′:4.5][1.2.4]thiazino[2.3-a]benzimidazol-13-ium tetrafluoroborate (3A); and
10-methoxy-3-(3-methoxy)propoxy-4-methyl-5H-pyrido[1′.2′:4.5][1.2.4]thiazino[2.3-a]benzimidazol-13ium tetrafluoroborate (3B) (isomeric mixture)

The aimed compound was obtained in the same manner as the one described in Example 1b.

m.p.: 149–151° C. (decomp.).

$^1$H-NMR(90MHz, CDCL$_3$-DMSO d$_6$) δ; 2.23(2H, m), 2.52(3H, s) 3.19(2H, t, J=6.3Hz), 3.36(3H, s), 4.10(3s), 4.58 (2H, t, J=6.3Hz), 4.88(2H, s), 6.76~7.80(4H, m), 9.40(1H, d, J=7.2Hz).

EXAMPLE 4

3-(3Methoxy)propoxy-2-methyl-5H-pyrido[1′.2′:4.5]-[1.2.4]thiazino[2.3-a]benzimidazol-13ium tetrafluoroborate The aimed compound was obtained in the same manner as the one described in Example 1b.

m.p.: 127°–130° C. (decomp.).

$^1$H-NMR(90MHz, CDCL$_3$-DMSO d$_6$) δ; 2.24(2H, m), 2.47(3H, s) 3.38(3H, s), 3.62(2H, t, J=6.3Hz), 4.68(2H, t, J=6.3Hz), 5.06(2H, s), 7.33~7.93(4H, m), 8.03(1H, s), 9.40(1H, s).

EXAMPLE 5

3-(3-Methoxy)propoxy-5H-pyrido[1′2′:4.5][1.2.4]-thiaziono[2.3-a]benzimidazol-13-ium tetrafluoroborate The aimed compound was obtained in the same manner as the one described in Example 1b.

m.p.: 90–95° C. (decomp.).

$^1$H-NMR(90MHz, CDCL$_3$-CD$_3$OD) δ; 1.96~2.36(2H, m), 3.36(3H, s) 3.62(2H, t, J=6.3Hz), 4.61(2H, t, J=6.3Hz), 4.96(2H, s), 7.46~8.12(6H, m), 9.39(1H, d, J=8.1Hz).

EXAMPLE 6

3-(4-Methoxy)butyloxy-4-methyl-5H-pyrido[1′2′:4.5][1.2.4.5][1.2.4]-thiaziazino[2.3-a]benzimidazol-13-ium tetrafluoroborate The aimed compound was obtained in the same manner as the one described in Example 1b.

m.p.: 161–164° C. (decomp.).

$^1$H-NMR(90MHz, CDCL$_3$-CD$_3$OD) δ; 1.58~2.16(4H, m), 2.52(3H, s) 3.36(3H, s), 3.48(2H, t, J=6.3Hz), 4.53(2H, t, J=6.3Hz), 4.88(2H, s), 7.22~7.82(4H, m), 7.73(1H, d, J=7.2Hz), 9.45(1H, d, J=7.2Hz).

EXAMPLE 7

2,4-Dimethyl-3-(3-methoxy)propoxy-5H-pyrido[1′2′:4.5]-[1.2.4]-thiaziazino[2.3-a]benzimidazol-13-ium tetrafluoroborate The aimed compound was obtained in the same manner as the one described in Example 1b.

m.p.: 103–108° C. (decomp.).

$^1$H-NMR(90MHz, CDCL$_3$-CD$_3$OD) δ; 1.90~2.30(2H, m), 2.62(6H, s) 3.38(3H, s), 3.60(2H, m), 4.60(2H, m) 4.89(2H, br), 7.20~7.82(4H, m), 9.52(1H, s).

EXAMPLE 8

9,10-3-[2-(2-methoxy)ethoxy]-4-methyl-5H-pyrido[1'.2':4.5][1.2.4]-thiaziazino[2.3-a]-benzimidazol-13-ium tetrafluoroborate

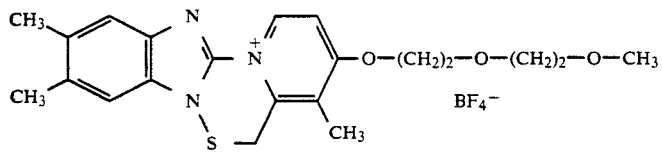

The aimed compound was obtained in the same manner as the one described in Example 1b.
m.p.: 154–155° C. (decomp.).
$^1$H-NMR(90MHz, CDCL$_3$-CD$_3$OD) δ; 2.36(3H, s), 2.40(3H, s) 2.53(3H, s), 3.38(3H, s), 3.65(4H, m), 3.90~4.10(2H, m), 4.56~4.78(2H, m), 4.86(2H, s), 7.20 (1H, s), 7.49(1H, s) 7.80(1H, d, J=7.2Hz), 9.42(1H, d, J=7.2Hz).

EXAMPLE 9A+9B

9-Chloro-3-[2-(2-methoxy)ethoxy]ethoxy-4-methyl-5H-pyrido[1'.2':4.5][1.2.4]thiaziazino[2.3-a]benzimidazol-13-ium tetrafluoroborate (9A); and
10-chloro-3-[2-(2-methoxy)ethoxy]ethoxy-4-methyl-5H pyrido[1'.2':4.5][1.2.4]thiaziazino[2.3-a]benzimidazol-13-ium tetrafluoroborate (9B) (isomeric mixture)

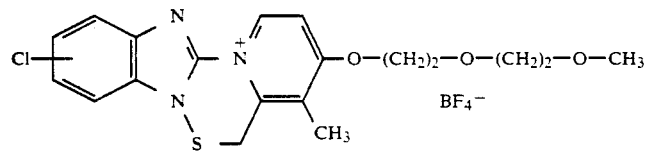

The aimed compound was obtained in the same manner as the one described in Example 1b.
m.p.: 147–149° C. (decomp.).
$^1$H-NMR(90MHz, CDCL$_3$-CD$_3$OD) δ; 2.54(3H, s), 3.36(3H, s) 3.66(4H, m), 3.88~4.10(2H, m), 4.56~4.81(2H, m), 5.03(2H, s), 7.24~7.98(4H, m), 9.52(1H, d, J=5.4Hz).

EXAMPLE 10

3-(3-Benzyloxy)propoxy-4-methyl-5H-pyrido[1'.2':4.5]-[1.2.4]thiaziazino[2.3-a]benzimidazol-13-ium tetrafluoroborate

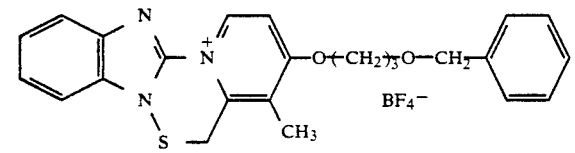

The aimed compound was obtained in the same manner as the one described in Example 1b.
m.p.: 147–149° C. (decomp).
$^1$H-NMR(90MHz, CDCL$_3$) δ; 2.22(2H, m), 2.40(3H, s) 3.68(2H, t, J=6.3 Hz), 4.51(2H, s), 4.61(2H, t, J=6.3Hz), 4.84(2H, s), 7.20~7.88(10H, m), 9.40(1H, d, J=7.2Hz).

EXAMPLE 11

3-(3-Hydroxy)propoxy-4-methyl-5H-pyrido[1'.2':4.5]-[1.2.4]thiaziazino[2.3-a]benzimidazol-13-ium tetrafluoroborate

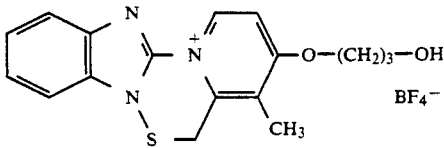

The aimed compound was obtained in the same manner as the one described in Example 1b.
m.p.: 149–151° C. (decomp.).
$^1$H-NMR(90MHz, CDCL$_3$-DMSO d$_6$) δ; 2.18(2H, m), 2.53(3H, s) 3.80(2H, t, J=6.3 Hz), 4.70(2H, t, J=6.3Hz), 5.01(2H, s), 7.33~7.99(4H, m), 7.87(1H, d, J=7.2Hz), 9.57(1H, d, J=7.2Hz).

EXAMPLE OF THE COMPOUND I-b

EXAMPLE 12

2-[2-(Ethyldithiomethyl)-4-(3-methoxy)propoxy-3-methyl-1pyridinio]benzimidazolide

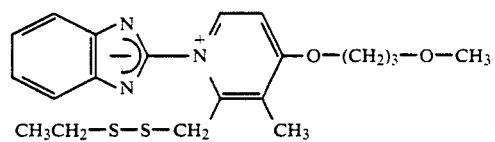

Process a: 1.0 g of 2-[4-(3-methoxy)-propoxy-3methylpyridin -2yl]methylsulfinyl-1H-benzimidazole sodium salt, 20 ml of acetone, 0.2 ml of ethyl mercaptan and 6 ml of 1 N hydrochloric acid were mixed together. The resulting mixture was stirred at room temperature for two hours and then the solvent was removed. A saturated aqueous solution of sodium hydrogencarbonate was added to the residue and the mixture was extracted with ethyl acetate. After drying over magnesium sulfate, the solvent was distilled off. Thus 0.91 g of the aimed compound was obtained in the form of yellow crystals.
Process b:
0.20 g of 3-(3-methoxy)propoxy-4-methyl-5H-pyrido[1'.2':4:5][1.2.4]thiaziazino[2.3-a]benzimidazol-13-ium tetrafuluoroborate, 2 ml of acetonitrile, 20 mg of ethyl mercaptan and 0.1 ml of 1N hydrochloric acid were mixed together. The obtained mixture was stirred at room temperature for five minutes. Then the reaction mixture was concentrated and a saturated aqueous solution of sodium hydrogencarbonate was added thereto. The resulting mixture was extracted with ethyl acetate. After drying over magnesium sulfate, the solvent was distilled off. Thus 0.15 g of the aimed compound (amorphous) was obtained in the form of yellow crystals.

$^1$H-NMR(90MHz, CDCL$_3$) δ; 1.00(3H, t, J=8.1Hz), 2.13(2H, m) 2.28(2H, m), 2.20(3H, s), 3.35(3H, s), 3.53 (2H, t, J=5.4Hz), 4.24(2H, t, J=5.4Hz) 4.82(2H, s), 6.71(1H, d, J=7.2Hz), 6.90 ~7.16(2H, m) 7.48~7.72(2H, m), 8.68 (1H, d, J=7.2Hz).

EXAMPLE 13

2-[2-(Ethyldithiomethyl)-4-(3-hydroxy)propoxy-3-methyl -1pyridinio]benzimidazolide

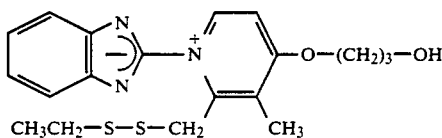

The aimed compound (amorphous) was obtained in the same manner as that described in Examples 12-a and 12-b.

$^1$H-NMR(90MHz, CDCL$_3$) δ; 1.00(3H, t, J=8.1Hz), 1.90~2.45(4H, m), 2.37(3H, s), 3.80(2H, t, J=5.4Hz), 4.29 (2H, t, J=5.4Hz), 4.74(2H, s), 6.90(1H, d J=7.2Hz), 6.98~7.20(2H, m), 7.46~7.70 (2H, m) 8.70(1H, d, J=7.2Hz).

We claim:
1. A pyridinium salt having the formula

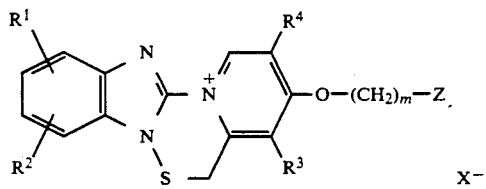

in which $R^1$ and $R^2$ each are hydrogen, a lower alkyl, a lower alkoxy, a halogenated lower alkyl, a lower alkoxycarbonyl, carboxyl or a halogen, $R^3$ and $R^4$ each are hydrogen or a lower alkyl, m is an integer of 2 to 10, Z is —OR$^5$ or —O—(CH$_2$)n—OR$^6$, $R^5$ and $R^6$ are hydrogen, a lower alkyl, an aryl or an aryl alkyl, n is an integer of 1 to 3 and X is a pharmacologically acceptable monovalent anion.

2. The pyridinium salt as claimed in claim 1 in which $R^3$ is methyl and $R^4$ is hydrogen.

3. The pyridinium salt as claimed in claim 1 in which $R^3$ is methyl, $R^4$ is hydrogen and Z is —OR$^5$.

4. The pyridinium salt as claimed in claim 1, in which $R^3$ is methyl, $R^4$ is hydrogen, Z is —OR$^5$ and m is 3.

5. The pyridinium salt as claimed in claim 1, in which $R^3$ is methyl, $R^4$ is hydrogen, Z is —OR$^5$, m is 3 and $R^5$ is methyl.

6. A pharmaceutical composition comprising a pharmacologically effective amount of the pyridinium salt as defined in claim 1 and a pharmacologically acceptable carrier or diluent.

* * * * *